(12) United States Patent
Mostafavi

(10) Patent No.: US 6,973,202 B2
(45) Date of Patent: Dec. 6, 2005

(54) SINGLE-CAMERA TRACKING OF AN OBJECT

(75) Inventor: Hassan Mostafavi, Los Altos, CA (US)

(73) Assignee: Varian Medical Systems Technologies, Inc., Palo Alto, CA (US)

( * ) Notice: Subject to any disclaimer, the term of this patent is extended or adjusted under 35 U.S.C. 154(b) by 345 days.

(21) Appl. No.: 10/234,658

(22) Filed: Sep. 3, 2002

(65) Prior Publication Data

US 2003/0063292 A1 Apr. 3, 2003

Related U.S. Application Data

(63) Continuation-in-part of application No. 09/893,122, filed on Jun. 26, 2001, which is a continuation-in-part of application No. 09/178,383, filed on Oct. 23, 1998, now Pat. No. 6,621,889, and a continuation-in-part of application No. 09/178,385, filed on Oct. 23, 1998, now Pat. No. 6,279,579, said application No. 09/893,122, is a continuation-in-part of application No. 09/712,724, filed on Nov. 14, 2000, now Pat. No. 6,690,965, which is a continuation of application No. 09/178,384, filed on Oct. 23, 1998, now abandoned.

(51) Int. Cl.$^7$ ............................................... G06K 9/00
(52) U.S. Cl. ........................................ 382/103; 382/154
(58) Field of Search ............................ 382/103, 107, 382/128, 131, 153, 154, 287, 291; 348/94, 142; 600/411, 414, 426, 427

(56) References Cited

U.S. PATENT DOCUMENTS

| | | | |
|---|---|---|---|
| 3,861,807 A | 1/1975 | Lescrenier | 356/152 |
| 3,871,360 A | 3/1975 | Van Horn et al. | 128/2.05 R |
| 3,952,201 A | 4/1976 | Hounsfield | 250/403 |
| 4,031,884 A | 6/1977 | Henzel | 128/2.05 R |
| 4,262,306 A | 4/1981 | Renner | 358/93 |

(Continued)

FOREIGN PATENT DOCUMENTS

| | | | |
|---|---|---|---|
| DE | 43 41 324 A1 | 6/1995 | A61B/17/22 |
| FI | 79458 B | 9/1989 | A61B/6/00 |
| WO | WO 98/16151 A1 | 4/1998 | A61B/5/0205 |
| WO | WO 98/38908 A1 | 9/1998 | A61B/5/00 |

OTHER PUBLICATIONS

International Search Report, Varian Medical Systems, Inc., PCT/US03/27552, Feb. 19, 2004.

Gerig, L.H., El Hakim, S.F., Szanto, J., Salhani, D., and Girard, A.,"The Development and Clinical Application of a Patient Position Monitoring System", Ottawa Regional Cancer Centre, General Division, 501 Smyth Rd., Ottawa, Ontario, Canada K1H 8L6; National Research Council, IIT, Ottawa, Ontario, Canada K1A OR6; *SPIE vol. 2350 Videometrics III* (1994); pp. 59–72.

(Continued)

*Primary Examiner*—Andrew W. Johns
(74) *Attorney, Agent, or Firm*—Bingham McCutchen LLP

(57) ABSTRACT

A method and system for determining the position and orientation of an object is disclosed. A set of markers attached or associated with the object is optically tracked and geometric translation is performed to use the coordinates of the set of markers to determine the location and orientation of their associated object.

30 Claims, 6 Drawing Sheets

U.S. PATENT DOCUMENTS

| | | | |
|---|---|---|---|
| 4,463,425 A | 7/1984 | Hirano et al. | 364/417 |
| 4,853,771 A | 8/1989 | Witriol et al. | 358/93 |
| 4,994,965 A | 2/1991 | Crawford et al. | 364/413.15 |
| 5,080,100 A | 1/1992 | Trotel | 128/653.1 |
| 5,271,055 A | 12/1993 | Hsieh et al. | 378/95 |
| 5,279,309 A | 1/1994 | Taylor et al. | 128/782 |
| 5,295,483 A | 3/1994 | Nowacki et al. | 128/660.03 |
| 5,315,630 A | 5/1994 | Sturm et al. | 378/65 |
| 5,389,101 A | 2/1995 | Heilbrun et al. | 606/130 |
| 5,394,875 A | 3/1995 | Lewis et al. | 128/660.09 |
| 5,446,548 A | 8/1995 | Gerig et al. | 356/375 |
| 5,538,494 A | 7/1996 | Matsuda | 600/1 |
| 5,582,182 A | 12/1996 | Hillsman | 128/716 |
| 5,603,318 A | 2/1997 | Heilbrun et al. | 128/630 |
| 5,622,187 A | 4/1997 | Carol | 128/897 |
| 5,662,111 A | 9/1997 | Cosman | 128/653.1 |
| 5,727,554 A | 3/1998 | Kalend et al. | 128/653.1 |
| 5,764,723 A | 6/1998 | Weinberger et al. | 378/65 |
| 5,771,310 A | 6/1998 | Vannah | 382/154 |
| 5,784,431 A | 7/1998 | Kalend et al. | 378/65 |
| 5,820,553 A | 10/1998 | Hughes | 600/426 |
| 5,823,192 A | 10/1998 | Kalend et al. | 128/845 |
| 5,836,954 A | 11/1998 | Heilbrun et al. | 606/130 |
| 5,954,647 A | 9/1999 | Bova et al. | 600/407 |
| 6,138,302 A | 10/2000 | Sashin et al. | 5/600 |
| 6,144,875 A | 11/2000 | Schweikard et al. | 600/427 |
| 6,146,390 A | 11/2000 | Heilbrun et al. | 606/130 |
| 6,165,181 A | 12/2000 | Heilbrun et al. | 606/130 |
| 6,185,445 B1 | 2/2001 | Knüttel | 600/411 |
| 6,185,446 B1 | 2/2001 | Carlsen, Jr. | 600/411 |
| 6,198,959 B1 | 3/2001 | Wang | 600/413 |
| 6,272,368 B1 | 8/2001 | Alexandrescu | 600/407 |
| 6,296,613 B1 | 10/2001 | Emmenegger et al. | 600/459 |
| 6,300,974 B1 | 10/2001 | Viala et al. | 348/61 |
| 6,348,058 B1 | 2/2002 | Melkent et al. | 606/130 |
| 6,434,507 B1 | 8/2002 | Clayton et al. | 702/152 |
| 6,501,981 B1 | 12/2002 | Schweikard et al. | 600/427 |
| 6,527,443 B1 | 3/2003 | Vilsmeier et al. | 378/205 |
| 6,611,617 B1 * | 8/2003 | Crampton | 382/154 |
| 6,724,930 B1 * | 4/2004 | Kosaka et al. | 382/154 |
| 2003/0210812 A1 * | 11/2003 | Khamene et al. | 382/128 |

OTHER PUBLICATIONS

Baroni, Guido; Ferrigno, Giancarlo, Real–time Motion Analysis for Definition and Control of Patient Position in Radiotherapy. *SPIE*, vol. 2709; 0–81942084–0/96; pp. 506–515.

Lopresti, B.J.; Russo, A., Jones, W.F., et al., "Implementation and Performance of an Optical Motion Tracking System for High Resolution Brain PET Imaging"; *IEEE Transactions on Nuclear Science*, vol. 46, No. 6, Dec. 1999; pp. 2065–2067.

Balter, J.M., et al.; "Uncertainties In CT–Based Radiation Therapy Treatment Planning Associated With Patient Breathing"; *Int. J. Radiat. Oncol., Biol., Phys.* 36; pp. 167–174 (Aug. 1996).

Bellenger, N.G., et al.; "Left Ventricular Quantification In Heart Failure By Cardiovascular MR Using Prospective Respiratory Navigator Gating: Comparison With Breath––Hold Acquisition"; *J. Magn. Reson. Imaging* 11; pp. 411–417; (Apr. 2000).

Cho, K., et al.; "Development Of Respiratory Gated Myocardial SPECT System"; *J. Nucl. Cardiol.* 6; pp. 20–28; (Jan./Feb. 1999).

Davies, S.C., et al.; "Ultrasound Quantitation Of Respiratory Organ Motion in The Upper Abdomen"; *Br. J. Radiol.* 67; pp. 1096–1102 (Nov. 1994).

Ehman, R.L., et al.; "Magnetic Resonance Imaging With Respiratory Gating: Techniques and Advantages"; *Am. J. Roentgenol* 143; pp. 1175–1182 (Dec. 1984).

Frölich, H., et al.; "A Simple Device For Breath–Level Monitoring During CT"; *Radiology* 156; p. 235 (Jul. 1985).

Hanley, J., et al.; "Deep Inspiration Breath–Hold Technique For Lung Tumors: The Potential Value of Target Immobilization And Reduced Lung Density In Dose Escalation"; *Int. J. Radiat. Oncol., Biol. Phys.* 45; pp. 603–611 (Oct. 1999).

Henkelman, R.M., et al.; "How Important Is Breathing In Radiation Therapy Of The Thorax?"; *Int. J. Radiat. Oncol., Biol., Phys.* 8; pp. 2005–2010 (Nov. 1982).

Hofman, M.B.M., et al.; "MRI Of Coronary Arteries: 2D Breath–Hold vs. 3D Respiratory–Gated Acquisition"; *J. of Comp. Assisted Tomography* 19; pp. 56–62 (Jan./Feb. 1995).

Iwasawa, T. et al.; "Normal In–Plane Respiratory Motion of the Bilateral Hemidiaphragms Evaluated By Sequentially Subtracted Fast Magnetic Resonance Images"; *Journal of Thoracic Imaging*; 1999; vol. 14, No. 2; pp. 130–134.

Johnson, L. S., et al.; "Initial Clinical Experience With A Video–Based Patient Positioning System"; *Int. J. Radiat. Oncol., Biol. Phys.* 45; pp. 205–213; (Aug. 1999).

Jolesz, F., M.D.; "Image–Guided Procedures and the Operating Room of the Future"; *Radiology; SPL Technical Report #48*; May 1997; 204: pp. 601–612.

Kachelriess, M., et al.; "Electrocardiogram–correlated Image Reconstruction From Subsecond Spiral Computed Tomography Scans Of The Heart"; *Med. Phys.* 25(12); Dec. 1998; pp. 2417–2431.

Keatley, E., et al.; "Computer Automated Diaphragm Motion Quantification in a Fluoroscopic Movie"; *Dept. of Medical Physics, Memorial Sloan–Kettering Cancer Center, New York; 3 pps.*.

Kim, W.S., et al.; "Extraction of Cardiac and Respiratory Motion Cycles by Use of Projection Data and Its Applications to NMR Imaging"; *Magnetic Resonance in Medicine* 13; 1990; pp. 25–37.

Korin, H.W., et al.; "Respiratory Kinematics Of The Upper Abdominal Organs: A Quantitative Study"; *Magn. Reson. Med.* 23; pp. 172–178 (Jan. 1992).

Kubo, H. D., et al.; "Breathing–Synchronized Radiotherapy Program at the University of California Davis Cancer Center"; *Med. Phys.* 27(2); Feb. 2000; pp. 346–353.

Kubo, H. D., et al.; "Potential and Role of a Prototype Amorphous Silicon Array Electronic Portal Imaging Device in Breathing Synchronized Radiotherapy"; *Med. Phys.* 26(11); Nov. 1999; pp. 2410–2414.

Kubo, H.D., et al.; "Compatibility Of Varian 2100C Gated Operations With Enhanced Dynamic Wedge And IMRT Dose Delivery"; *Med. Phys.* 27; pp. 1732–1738; (Aug. 2000).

Kubo, H. D., et al., "Respiration Gated Radiotherapy Treatment: A Technical Study"; *Phys. Med. Biol.* (1996) vol. 41; pp. 83–91.

Kutcher, G.J., et al.; "Control, Correction, and Modeling Of Setup Errors and Organ Motion", *Semin. Radiat. Oncol.* 5; pp. 134–145 (Apr. 1995).

Lethimonnier, F., et al.; "Three–Dimensional Coronary Artery MR Imaging Using Prospective Real–Time Respiratory Navigator And Linear Phase Shift Processing: Comparison With Conventional Coronary Angiography"; *Magn. Reson. Imaging* 17; pp. 1111–1120; (1999).

Lewis, C.E., et al.; "Comparison Of Respiratory Triggering And Gating Techniques For The Removal Of Respiratory Artifacts In MR Imaging"; *Radiology* 160; pp. 803–810; (Sep. 1986).

Li, D., et al.; "Coronary Arteries: Three–dimensional MR Imaging With Retrospective Respiratory Gating"; *Radiology*; Dec. 1996; vol. 201; No. 3.; pp. 857–863.

Luker, G. D., et al.; "Ghosting of Pulmonary Nodules With Respiratory Motion: Comparison of Helical and Conventional CT Using an In Vitro Pediatric Model"; *AJR:167*; Nov. 1996; pp. 1189–1193.

Mageras, G., et al.; "Initial Clinical Evaluation Of A Respiratory Gating Radiotherapy System"; $22^{nd}$ *Annual EMBS International Conference, Chicago, IL.*; pp. 2124–2127; (Jul. 23–28, 2000).

Mageras, G.S., et al.; "Respiratory Motion–Induced Treatment Uncertainties"; *Patras Medical Physics 99—VI International Conference On Medical Physics, Monduzzi Editore*; pp. 33–39; (Sep. 1999).

Mageras, G.S.; "Interventional Strategies For Reducing Respiratory–Induced Motion In External Beam Therapy"; *The Use of Computers In Radiation Therapy XIIIth International Conference, Heidelberg, Germany*; pp. 514–516; (May 2000).

Mah, D., et al.; "Technical Aspects Of The Deep Inspiration Breath Hold Technique In The Treatment Of Thoracic Cancer"; *Int. J. Radiat. Oncol., Biol., Phys.* 48; pp. 1175–1185; (Nov. 2000).

Mah, K., et al.; "Time Varying Dose Due To Respiratory Motion During Radiation Therapy Of The Thorax"; *Proceedings of the Eighth Int'l Conference on the Use of Computers In Radiation Therapy*; Toronto, Canada; Jul. 9–12, 1984; pp. 294–298.

Malone, S., et al.; "Respiratory–Induced Prostate Motion: Quantification And Characterization", *Int. J. Radiat. Oncol., Biol., Phys.* 48; pp. 105–109; (Aug. 2000).

Moerland, M.A., et al.; "The Influence Of Respiration Induced Motion Of The Kidneys On The Accuracy Of Radiotherapy Treatment Planning, A Magnetic Resonance Imaging Study"; *Radiotherapy Oncol.* 30, pp. 150–154 (1994).

Mori, M., et al.; "Accurate Contiguous Sections Without Breath–Holding On Chest CT: Value of Respiratory Gating and Ultrafast CT"; *AJR:162*, May 1994; pp. 1057–1062.

Ohara, K., et al.; " Irradiation Synchronized With Respiration Gate"; *Int. J. Radiat. Oncol., Biol. Phys.* 17; pp. 853–857; (Oct. 1989).

Oshinski, J.N., et al.; "Two–Dimensional Coronary MR Angiography Without Breath Holding"; *Radiology* 201; pp. 737–743; (Dec. 1996).

Peltola, S.M..; "Gated Radiotherapy To Compensate For Patient Breathing"; *Proceedings of the Eleventh Varian Users Meeting*; Marco Island, Florida; May 11–13, 1986.

Ramsey, C.R., et al.; "A Comparison Of Beam Characteristics For Gated And Nongated Clinical X–Ray Beams"; *Med. Phys.* 26; pp. 2086–2091; (Oct. 1999).

Ramsey, C.R., et al.; "Clinical Efficacy Of Respiratory Gate Conformal Radiation Therapy"; *Med. Dosim.* 24; pp. 115–119; (1999).

Ritchie, C. J., et al.; "Predictive Respiratory Gating: A New Method To Reduce Motion Artifacts on CT Scans"; *Radiology*; 1994; pp. 847–852; vol. 190; No. 3.

Robinson, T.E., et al.; "Standardized High–Resolution CT of the Lung Using A Spirometer–Triggered Electron Beam CT Scanner"; *AJR:172*; Jun. 1999; pp. 1636–1638.

Rogus, R.D., et al.; "Accuracy Of A Photogrammetry–Based Patient Positioning and Monitoring System For Radiation Therapy"; *Med. Phys.* 26; pp. 721–728; (May 1999).

Rosenzweig, K.E., et al.; "The Deep Inspiration Breath Hold Technique In The Treatment Of Inoperable Non–Small Cell Lung Cancer"; *Int. J. Radiat. Oncol., Biol., Phys.* 48; pp. 81–87; (Aug. 2000).

Ross, C.S., et al.; "Analysis Of Movement Of Intrathoracic Neoplasms Using Ultrafast Computerized Tomography"; *Int. J. Radiat. Oncol., Biol., Phys.* 18; pp. 671–677; (Mar. 1990).

Runge, V.M., et al.; "Respiratory Gating In Magnetic Resonance Imaging at 0.5 Tesla"; *Radiology* 151; pp. 521–523; (May 1984).

Sachs, T.S., et al.; "Real–Time Motion Detection In Spiral MRI Using Navigators"; *Magn. Reson. Med.* 32; pp. 639–645; (Nov. 1994).

Schwartz, L.H., et al.; "Kidney Mobility During Respiration"; *Radiother. Oncol.* 32; pp. 84–86; (1994).

Shirato, H., et al.; "Four–Dimensional Treatment Planning And Fluroscopic Real–Time Tumor Tracking Radiotherapy For Moving Rumor"; *Int. J Radiat. Oncol., Biol., Phys.* 48; pp. 435–442; (Sep. 2000).

Sinkus, R., et al.; "Motion Pattern Adapted Real–Time Respiratory Gating"; *Magnetic Resonance in Medicine* 41; 1999; pp.148–155.

Solberg T. D., et al.; "Feasibility of Gated IMRT"; 3 pps., not dated.

Suramo, M. P., et al.; "Cranio–caudal Movements Of The Liver, Pancreas And Kidneys In Respiration", *Acta Radiol. Diagn.* 2; pp. 129–13 1; (1984).

Tada, T., et al.; "Lung Cancer: Intermittent Irradiation Synchronized With Respiratory Motion–Results Of A Pilot Study"; *Radiology*; Jun., 1998; vol. 207; No. 3; pp. 779–783.

van Geuns, R.J., et al.; "Magnetic Resonance Imaging Of The Coronary Arteries: Clinical Results From Three Dimensional Evaluation Of A Respiratory Gated Technique"; *Heart* 82; pp. 515–519; (Oct. 1999).

Wang, Yi, et al.; "Implications For The Spatial Resolution in Coronary Imaging"; *Magnetic Resonance in Medicine* 33; 1995; pp. 713–719.

Weiger, M., et al.; "Motion–Adapted Gating Based on k–Space Weighting For Reduction of Respiratory Motion Artifacts"; *Magnetic Resonance in Medicine* 38; 1997; pp. 322–333.

Wong, J. W., et al.; "The Use Of Active Breathing Control (ABC) To Reduce Margin For Breathing Motion"; *Int. J. Radiation Oncology Biol. Phys.*; 1999; vol. 44; No. 4; pp. 911–919.

Woodard, P. K., et al.; "Detection of Coronary Stenoses on Source and Projection Images Using Three–Dimensional MR Angiography With Retrospective Respiratory Gating: Preliminary Experience"; *AJR:170*; Apr. 1998; No. 4; pp. 883–888.

Yorke, E., et al.; "Respiratory Gating Of Sliding Window IMRT"; $22^{nd}$ Annual EMBS International Conference, Chicago, IL.; pp. 2118–2121; (Jul. 23–28, 2000).

Yuan, Q., et al.; "Cardiac–Respiratory Gating Method For Magnetic Resonance Imaging Of The Heart"; *Magn. Reson. Med.* 43; pp. 314–318; (Feb. 2000).

* cited by examiner

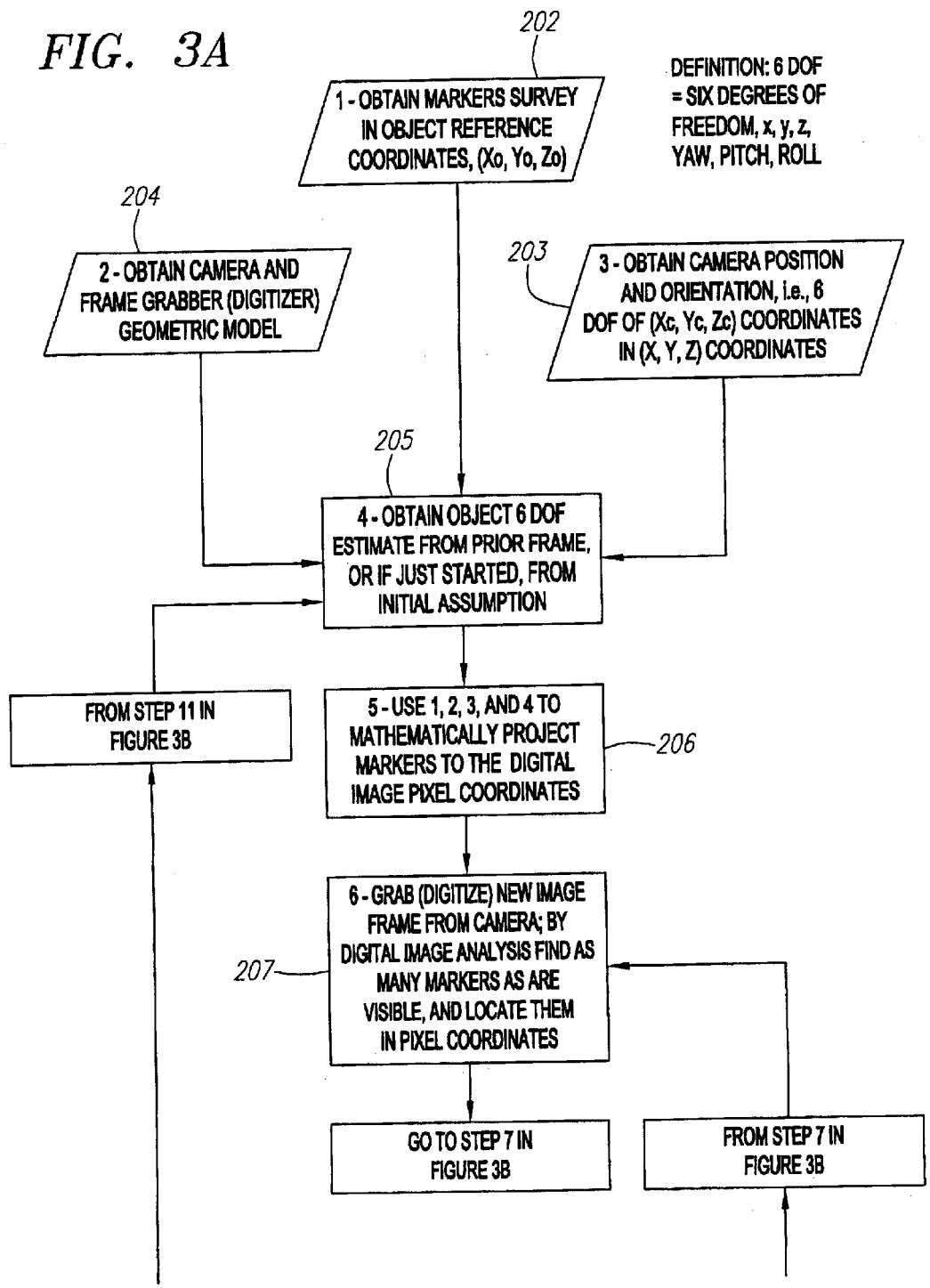

SINGLE-CAMERA TRACKING OF AN OBJECT

CROSS-REFERENCE TO RELATED APPLICATIONS

The present application is a continuation-in-part of U.S. application Ser. No. 09/893,122, filed Jun. 26, 2001, which is continuation-in-part of U.S. application Ser. Nos. 09/178,383 filed Oct. 23, 1998 now U.S. Pat. No. 6,621,389, and is a continuation in part of 09/178,385, filed Oct. 23, 1998, now U.S. Pat. No. 6,279,579, issued on Aug. 28, 2001, and is a continuation in part of 09/712,724 filed Nov. 14, 2000, now U.S. Pat. No. 6,690,965, which is a continuation of U.S. application Ser. No. 09/178,384 filed Oct. 23, 1998, now abandoned.

BACKGROUND AND SUMMARY

The present invention relates to methods and systems for determining the position and orientation of an object in 3-dimensional space.

There are many applications where detection and tracking of the location and orientation of an object is desired. One approach for accomplishing this involves using multiple cameras to determine the location of a specific point in space via triangulation. The orientation of an object can be determined using triangulation by finding the position of multiple points that have a known geometry on the object. A drawback to the multiple-camera procedure is the increase in cost. Another is the physical space requirements of the system.

Another procedure for finding the position of a point in space involves the use of magnetic fields and magnetic field detectors to sense the location of the detectors. Another method uses sonic wave sources located on the object and multiple detectors to locate the sources in 3D space. Another approach involves the use of an extendable multi-segment arm that is planted at one end at a fixed location. Rotation sensors measure the rotation of each segment relative to the adjacent segment thus enabling calculation of the position and orientation of the end of the arm. In this approach, the object to be tracked is attached to the end of the extendable arm. The sonic approaches suffer from unstable calibration that drifts regularly with ambient air conditions such as temperature and humidity. The magnetic field approach has inaccurate calibration because of changeable geometry of large metallic objects that distort the magnetic fields. All of these approaches including the mechanical arm require tethering the sensors, i.e., electrical and/or mechanical connection from the sensor to a processing unit. This contrasts with optical tracking such as the subject of this invention that are non-contact and measure the location and orientation of an object from a stand-off position.

A specific application where the position and orientation of an object is desired is in the insertion of surgical instruments, such as a biopsy needle into a patient or positioning of an ultrasound imaging probe on the patient. During many of these procedures, the practitioner cannot visualize the position of the instrument or the image produced by the probe in a known reference that would allow position sensing relative, for example, to an internal organ.

According to one embodiment, the invention provides improved methods and systems for the detection and tracking of objects in 3-dimensional space. Reference points of known distances and geometries relative to each other are located, allowing for the determination of the location of any point or orientation of any line whose location and orientation is known relative to the reference points. In an embodiment, an optical-based system employing the use of one or more cameras is used to locate the reference points. An aspect of this embodiment involves placing markers at the reference points and using a computing device to compute the location of the markers and the orientation of a device on which the markers are fixed. According to an embodiment, a method for determining the location of the markers comprises viewing the markers with at least one camera, producing an image of the markers, finding pixel coordinates of the markers, and using reference data to compute the locations of the markers from the pixel coordinates.

An embodiment of the invention also provides a method and system for the digitization of a 3-dimensional curve that is traced with a pointer device. In a specific application, the pointer device can be used for patient profiling.

Another embodiment of the invention provides a method and system for digitizing the position and orientation of a surgical instrument. According to an embodiment, the position and orientation of the surgical instrument is determined in the same coordinate system as an image of a patient internal organs produced by a 3D imaging method such as CT, MRI or PET.

These and other aspects, objects, and advantages of the invention are described below in the detailed description, drawings, and claims.

BRIEF DESCRIPTION OF THE DRAWINGS

The accompanying drawings are included to provide a further understanding of the invention and, together with the Detailed Description, serve to explain the principles of the invention.

FIGS. 3a and 3b are flowcharts showing process actions performed in an embodiment of the invention;

DETAILED DESCRIPTION

Figure 1:
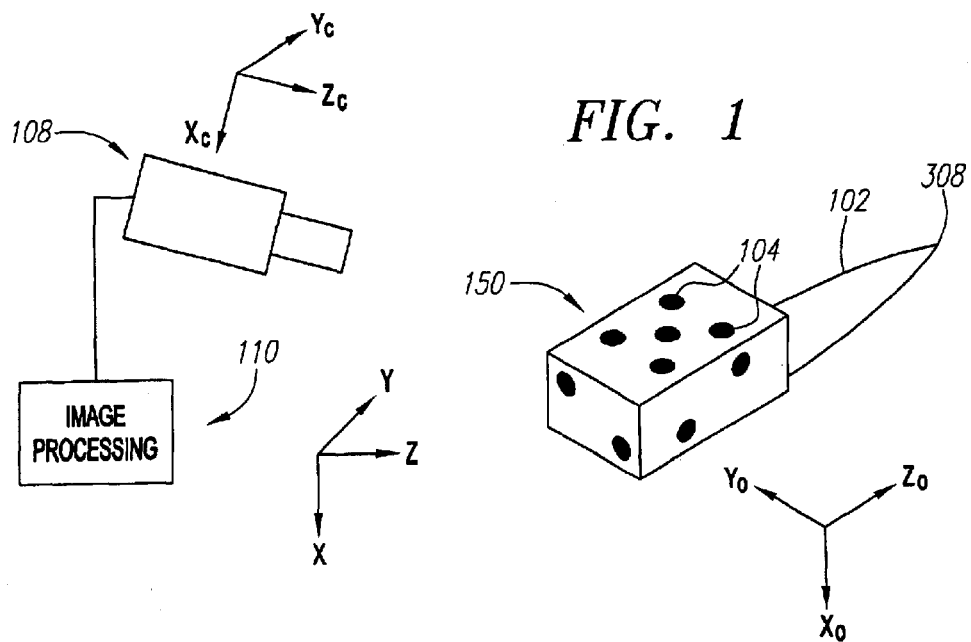
FIG. 1 depicts the components of a system for single-camera object position and orientation tracking according to an embodiment of the invention.

FIG. 1 depicts components of an embodiment of a system for detecting the position and orientation of an object or instrument 102. The object 102 comprises or is rigidly attached to a marker block 150 having three or more markers 104 located thereon or therein. An optical or video image apparatus, such as video camera 108, is aimed such that at least part of the marker block 150 is within the camera's field of view. Surfaces on marker block 150 include a combination of three or more markers that is or can be rendered visible to camera 108. The output data from camera 108 is sent to an image processing unit 110, which in one embodiment, comprises an analog/digital converter to generate digital pixel data, as well as a processor and storage components to manipulate, process, and store the image data.

According to an embodiment, camera 108 is placed on the ceiling, wall, or other support structure with its pointing angle adjusted to cover the working volume of interest. For purposes of illustration only, a single camera 108 is shown in FIG. 1. However, the number of cameras 108 employed in the present invention can exceed that number to increase the field of view.

As stated above, the object 102 is rigidly attached to or is formed as part of the marker block 150. Therefore, the position of any point of object 102 can be absolutely known or measured relative to the marker block 150. By identifying the position and orientation of marker block 150, the position or orientation of any point on object 102 can also be calculated.

Figure 2A:
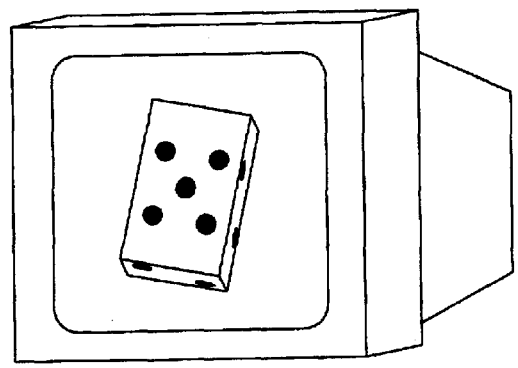
FIGS. 2a and 2b depict examples of image frames showing a marker block at different orientations according to an embodiment of the invention.
Figure 2B:
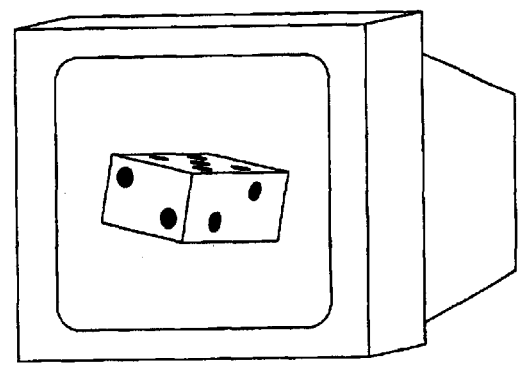

A high level description of an embodiment of the invention will now be provided. The camera 108 is used to capture a video image of the marker block 150. When a single camera approach is employed, a subset of at least three markers 104 should be visible to the camera 108. However, the specific combination of markers 104 that is visible at any moment in time may change between images obtained by the camera 108. This principle is illustrated in FIGS. 2a–b. FIG. 2a illustrates an image frame that captures an image of marker block 150, at a moment in which the marker block 150 is oriented relative to the camera 108 such that only the top surface of marker block 150 is visible. Therefore, only the markers on the top surface of marker block 150 can be clearly identified in the image frame. FIG. 2b illustrates an image frame that captures an image of marker block 150, at a moment in which the marker block 150 is oriented relative to the camera 108 such that only two sides of the marker block 150 are visible. Therefore, only the markers on the two visible sides of the marker block 150 can be clearly identified in the image frame.

The combinations of locations of markers 104 on the marker block 150 can be surveyed to provide information about the relative positioning of markers 104 on marker block 150. The position and orientation of the camera 108 can also be calibrated. By identifying the specific combinations and locations of markers 104 that are visible in a given image frame, the present invention can be used to determine the position and orientation of the marker block 150. The position and orientation of the marker block can be identified using six degrees of freedom (6 DOF), i.e., x-coordinate, y-coordinate, z-coordinate, pitch, yaw, and roll. With this information, the position and orientation of any point on the object 102 rigidly attached to the marker block 150 can also be identified. As previously noted, this approach allows only a single camera 108 to be used to track the position and orientation of the object 102, rather than requiring triangulation using multiple cameras from different positions.

Figure 3B:
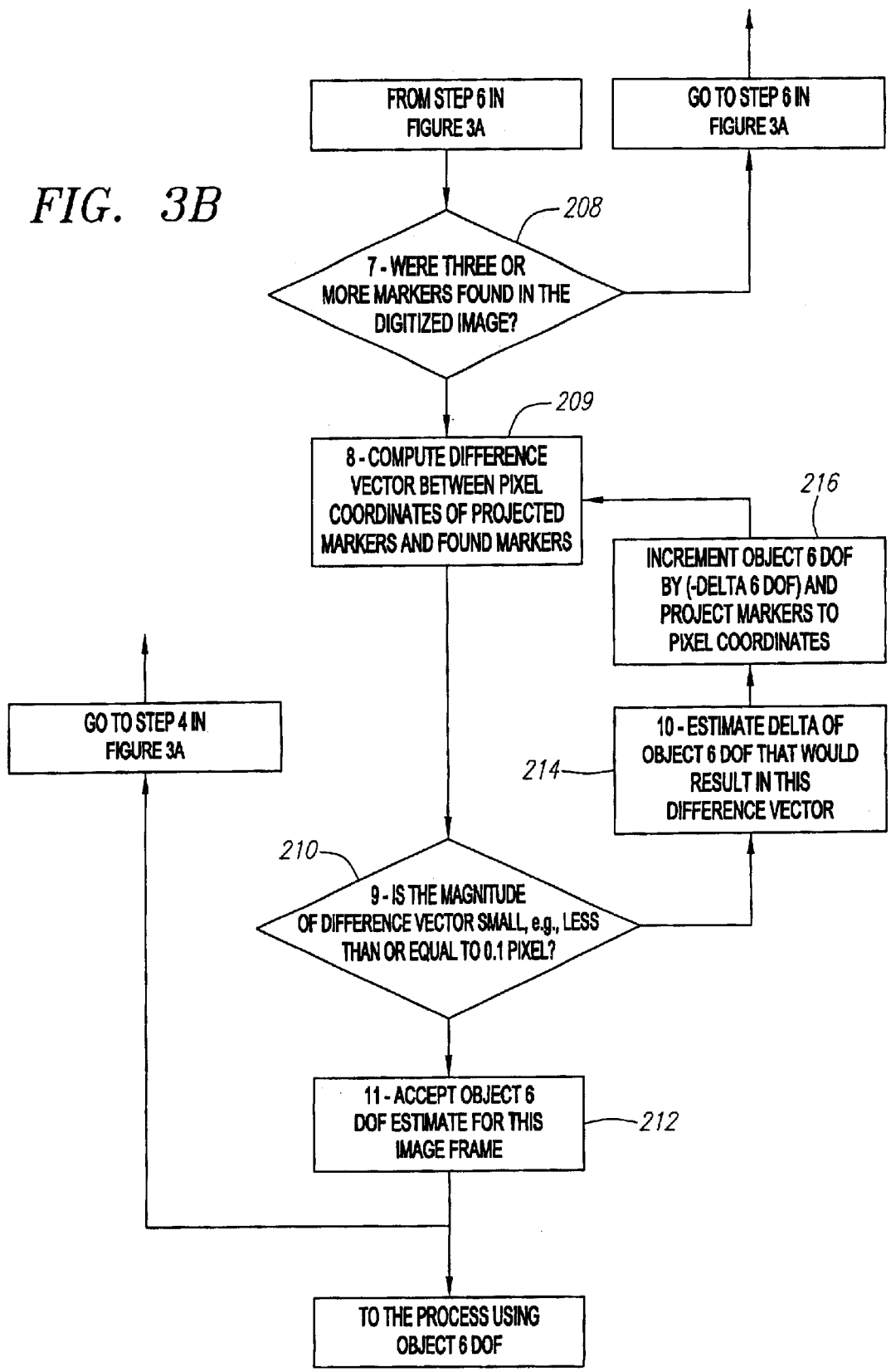

FIGS. 3a and 3b taken together show a flowchart of a process for object 6 DOF estimation according to one embodiment of the invention. At 202, the coordinates of the markers 104 are accurately surveyed in a reference coordinate system ($x_o$, $y_o$, $z_o$) specific to the marker block 150. This survey data is stored as reference data, and provides the known relative positioning and distances between markers 104 on the marker block 150. The known relative positioning and distances between relevant portions of object 102 and one or more markers 104 or marker block 150 can also identified at this stage.

At 203, The position and orientation of the camera 108 is calibrated using coordinate data related to the 6 DOF for camera 108. Thus, the coordinates ($x_c$, $y_c$, $z_c$) for camera 108 can be translated and rotated relative to the coordinates (x, y, z) for the entire system. The system coordinates can be derived based upon any frame of reference, e.g., relative to the system isocenter of an appropriate medical treatment/imaging device or of the room coordinates. One approach for performing this calibration is to use the camera to image a structure at a known location having one or more structures of known relative dimensions/distances, e.g., a block structure having rods of known heights and relative positions. The size, orientation, and position of the known structure in the image frame captured by the camera can be used to extrapolate and calibrate the 6 DOF values for the camera.

At 204, the geometric calibration model of the overall imaging chain is obtained and stored. The parameters of this model relate the position of a point in a 3-dimensional measurement coordinate system to the 2-dimensional pixel coordinates of an image obtained by the camera 108. In one embodiment, this reference data and geometric calibration model for steps 202, 203 and 204 can be derived offline, e.g., after the camera 108 is mounted rigidly in a room, and can be repeated for accuracy verification.

At 205, an initial set of image data is obtained. The initial set of data provides an initial estimate of the location and orientation for the marker block 150. Thus, the initial set of data can be obtained from a prior image frame. Alternatively, the initial set of data can be manufactured based upon an initial estimate of the expected image frame data for the marker block 150.

At 206, the marker information for the initial set of data is projected to the pixel domain. Using the information obtained from the process shown in FIG. 3a, the position and distance in pixel coordinates between the markers 104 in the initial set of image data is compared with the calibration model, such that the absolute positions of the markers 104 in the measurement coordinate system can be estimated with a high degree of accuracy. The estimated image frame, the geometric calibration model, and the marker reference data are used to mathematically project the center of each marker 104 and obtain estimated pixel coordinates of each marker 104 in the image frame. This provides the pixel coordinates for the estimated 6 DOF values for the marker block 150 in the initial set of data.

At 207, a new image frame is digitized from the camera 108 video stream. The digitized image frame is analyzed to detect and locate the markers 104 in pixel coordinates. If the previous tracking was successful, the projected centers can be used to limit the search area for each marker 104 to increase computational efficiency. If processing the first image frame, or recovering from lost track, then the whole frame can be analyzed to find and locate markers 104.

A determination is made at 208 whether at least three markers 104 can be identified in the acquired image frame. If not, then 207 is repeated to obtain another image frame.

A difference vector is formed between the projected marker coordinates (of step 206) and the marker coordinates found in the grabbed image frame. At 210, the absolute value of the difference vector, e.g., measured in mean of squared distances in pixel domain, is analyzed to determine if it falls within an acceptable threshold amount. In effect, a determination is made whether the 6 DOF for the initial estimate is close enough to the actual 6 DOF for the marker data in the grabbed image frame. If so, then the 6 DOF data from the initial estimate is accepted as the coordinates for the marker block (212). Thereafter, the position and orientation of the object 102 can be extrapolated based upon the computed positions for markers 104. As mentioned above, the position and orientation of the object 102 can be quantified in 6 DOF, e.g., x-coordinate, y-coordinate, z-coordinate, pitch, yaw, and roll in the measurement coordinate system. The process then returns to step 205 for the next image frame in the video stream.

If the difference between the mathematically projected pixel coordinates and the actual marker 104 pixel coordinates exceeds a defined threshold, then the process revises the estimated coordinates for the markers 104. The new estimated coordinates can be estimated based upon incremental changes to the assumed marker block 150 6 DOF that would result in a closer match between the mathematically projected points and the marker 104 coordinates found in the actual digitized image. One approach for this estimation uses the Gauss method based on computing the inverse Jacobian matrix of pixel positions as a function of the marker block 150 6 DOF. A Δ6 DOF can be determined and applied to revise the estimated 6 DOF values for the markers. The revised estimated 6 DOF values are again projected to the pixel domain at 216. The process loops back to 209/210 to generate another difference vector and to make another determination whether the difference vector is within an acceptable threshold. If not, then the loop is repeated until the difference vector satisfies the defined threshold value. If it is detected convergence is not happening, a failed 6 DOF estimation is declared and the process goes to Step 6 (207) for a new image frame.

Figure 4:
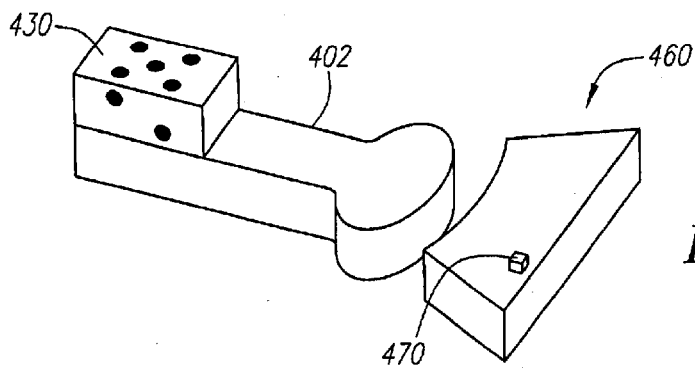
FIG. 4 shows an application of the invention to detect the position and orientation of an ultrasound imaging probe.

FIG. 4 depicts a particular application of the invention, in which a marker block 450 is rigidly attached to an ultrasound probe 402. Using the process described with respect to FIGS. 3a and 3b, the position and orientation of ultrasound probe 402 can be identified with precision, even while it is flexibly being used to image a patient or object. In an embodiment, particular structures that are being imaged by the ultrasound probe can also be translated into the system measurement coordinate system. This can be accomplished by pre-calibrating the ultrasound probe to translate positions for measured voxels 470 in the image data to the coordinate system being used by the ultrasound probe. One way of accomplishing this is to apply the ultrasound probe to image a set of reference objects of known position relative to the ultrasound probe. The resultant mapping information is used as reference data to later translate voxel positional information into the coordinate system used by the ultrasound probe. Once the process of FIGS. 3a and 3b has determined the position and orientation of ultrasound probe 402, the invention can further extrapolate the position and orientation of particular voxels 470 and structures within field of view 460 of the ultrasound probe 402.

Figure 9:
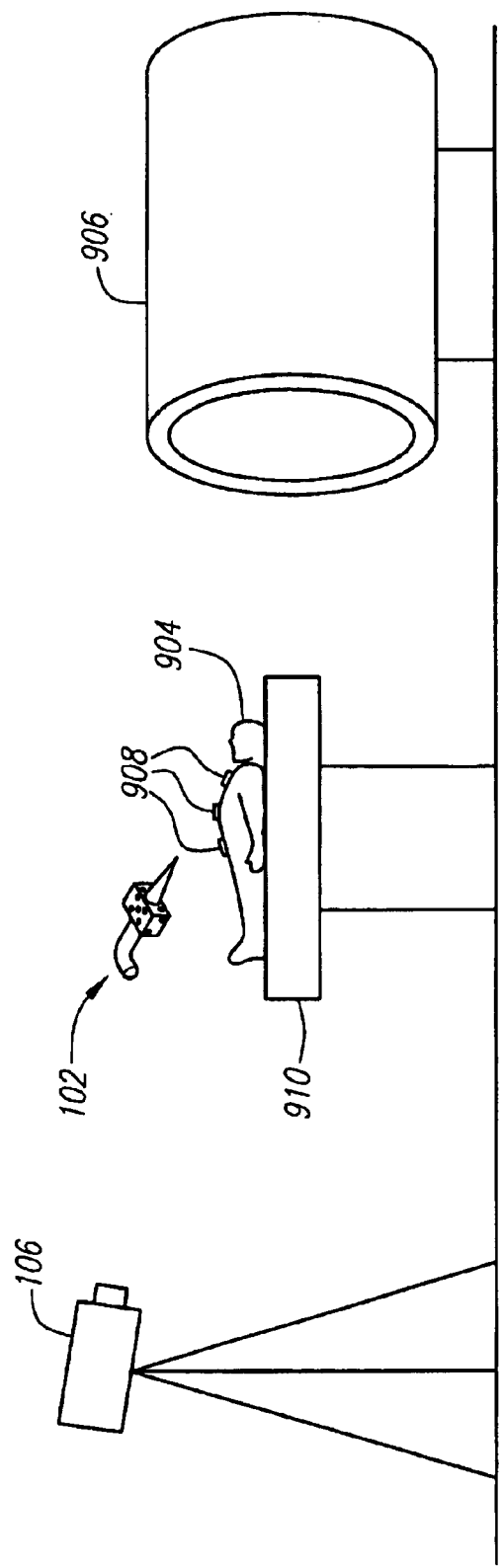
FIG. 9 shows an application of the invention to a surgical instrument embodiment of the invention.

FIG. 9 depicts another application of the invention, in which object 102 comprises a surgical instrument. In this embodiment, a relevant portion of the patient 904 is first imaged, e.g., with an instrument 906 that utilizes a 3D imaging method, e.g., computed tomagraphy (CT), magnetic resonance imaging (MRI), or positron emission tomography (PET). The 3D imaging method produces a 3-dimensional image of at least a portion of the patient's 904 body in an imaging coordinate system. The geometric calibration model that defines the measurement coordinate system (i.e. "room coordinates") obtained in step 204 is defined such that it coincides with the imaging coordinate system. The image of the patient's body allows precise planning for a surgical procedure. The surgical instrument 102 can be guided during a surgical procedure based upon either a pre-determined treatment plan or in real-time based upon knowledge of absolute and/or relative positions for relevant positions of the patient's body. As long as the position of the patient's 904 body is appropriately similar to the position utilized during the 3D imaging method, the position and orientation of the surgical instrument determined in the measurement coordinate system will accurately reflect the position and orientation relative to the portion of the patient's 904 body that was imaged by instrument.

It is noted that the invention can be applied to determine the position and orientation of the patient's 904 body using only a single camera. For example, during the 3D imaging method, the position and orientation of the patient 904 can be accurately determined by utilizing one or more marker blocks 908 affixed or attached to the patient's 904 body. Each marker block 908 contains a plurality of markers that can be imaged with camera 108. Using a procedure as described with respect to FIGS. 3a–b, the position and orientation of the marker block 908 can be determined from images taken by camera 108. The position and orientation of patient 904 can be extrapolated using the determined position and orientation of marker block(s) 908.

The invention can further be used to determine if the patient 904 has moved from a previous position or orientation. For example, it is possible that the date of the 3D imaging procedure is different than the date at which the patient undergoes a surgical procedure reliant upon that imaging information. However, if the treatment plan was created with the assumption that the patient would be in the same position or orientation, then the treatment effectiveness could be compromised if the patient is actually in a different position or orientation during the later date of the surgical procedure. If the patient 904 has moved after the 3D imaging method and prior to a surgical procedure to be performed with surgical instrument, the patient 904 and/or the patient table 910 can be repositioned so that the patient's 904 body is returned to the same position. The repositioning is accomplished by placing one or more marker blocks 908 on the same body landmarks, and moving the patient 904 and/or the patient table 910 until the position and orientation of the marker blocks 908 as determined from images taken by camera 108 match the position and orientation recorded during the 3D imaging method. A procedure for manipulating a patient into a correct position and orientation is described U.S. Pat. No. 6,279,579, which is hereby incorporated by reference in its entirety.

Figure 8:
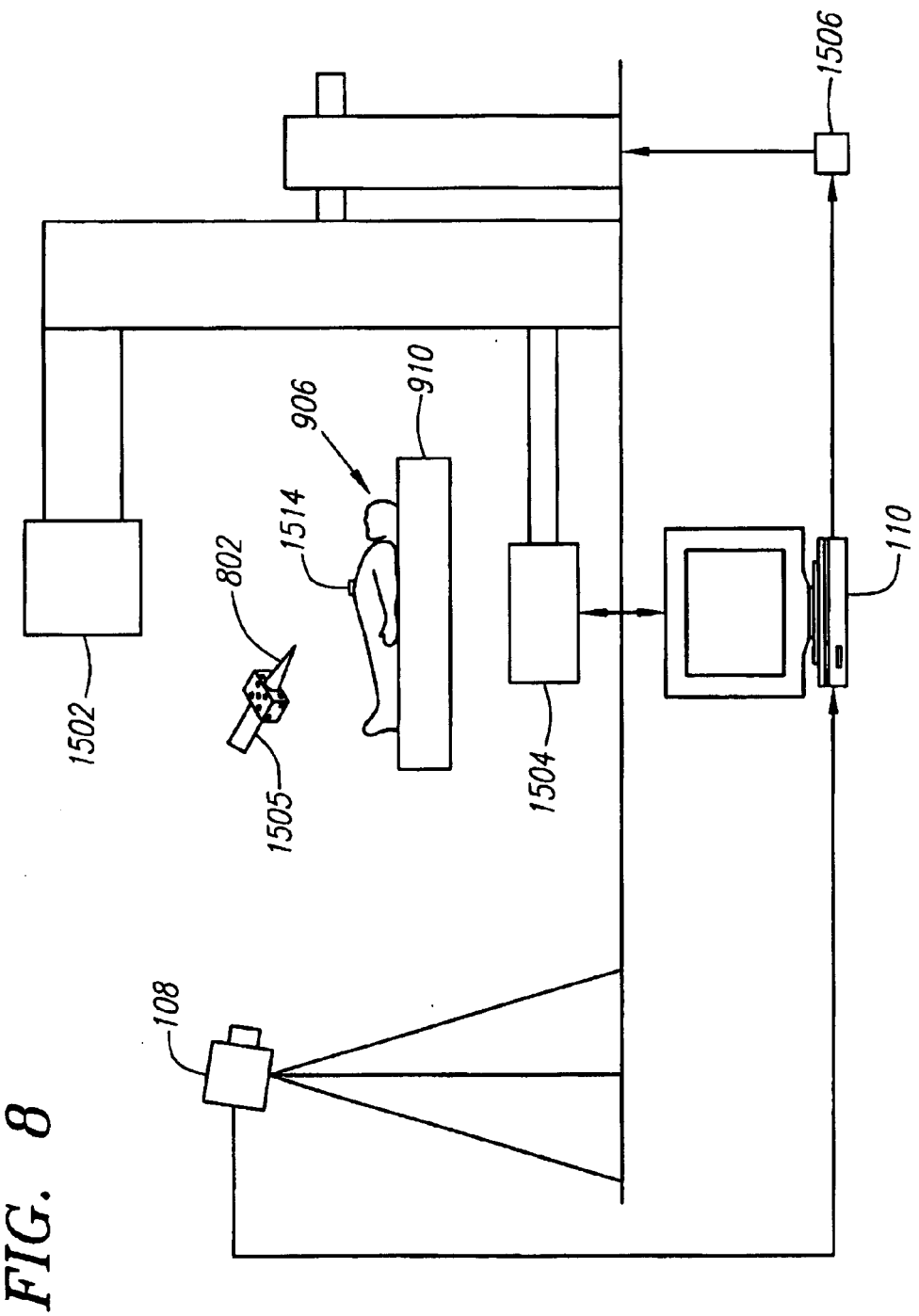
FIG. 8 depicts an image guided surgery according to an embodiment of the invention.

FIG. 8 depicts an embodiment of a system in which internal images of the patient 906 can be captured during the surgical procedure. The images can be captured in real-time or periodically. The system shown in FIG. 8 includes an x-ray source device 1502 and an x-ray imaging device 1504. Image-guided surgery can be performed in which the positions of surgical instrument 802 is determined using the optical approach described above, and in which real-time internal images are obtained simultaneously or in a coordinated fashion to guide the use of the surgical instrument 802.

Even if the patient's 904 body maintains the same position as that assumed during the 3D imaging method, locations within the patient's 904 body can move with variations in the patient's 904 physiological activities, such as breathing. Such movement will cause a deviation in internal positions within the patient's 904 body from the positions recorded in the image obtained with the 3D imaging method. The tracking of the position and orientation of marker blocks 908 can provide monitoring of physiological activities such as by tracking chest movement or movement of internal structures. In the system shown in FIG. 8, a first switch 1505 or alarm can be operatively coupled to the surgical instrument 802. A second switch 1506 is operatively coupled to a radiation source 1502. Either switch can be operated to suspend its corresponding surgical/medical procedure if excessive movement of the patient 906 is detected. In an embodiment, switch 1506 is part of the mechanical and electrical structure of radiation beam source 1502, and switch 1505 is part of the mechanical and electrical structure of the control arm for the surgical instrument 802. Alternatively, switches 1505 and 1506 comprise external apparatuses that are connected to the control electronics/mechanics of their associated instruments. Switches 1505 and 1506 may also comprise software-based control mechanisms.

While the processes of FIGS. 3a and 3b is usable with only a single camera 108, multiple cameras can also be used to expand the viewing volume, or to allow continued operation of the system when the view of one camera 108 is obstructed. When multiple cameras are used, the above process can be employed for each camera 108, independently, or triangulation of image data can alternatively be used to provide coordinates for the markers 104.

A possible inefficiency in locating the markers 104 is that the markers 104 may appear anywhere on the video frame, and all of the image elements of the video frame may have to be examined to determine the location of the markers 104. Thus, in an embodiment, the initial determination of locations for the markers 104 involves an examination of all of the image elements in the video frame. If the video frame comprises 640 by 480 image elements, then all 307200 (640×480) image elements are initially examined to find the location of the markers 104.

For real-time tracking of the markers 104, examining every image element for every video frame to determine the location of the markers 104 in real-time could consume a significant amount of system resources. Thus, in an embodiment, the real-time tracking of markers 104 can be facilitated by processing a small region of the video frame, referred to herein as a "tracking gate", that is placed based on estimation of the location of the already-identified markers 104 in a previous video frame. The previously determined location of a marker 104 defined in the previous video frame is used to define an initial search range (i.e., the tracking gate) for that same marker 104 in real-time. The tracking gate is a relatively small portion of the video frame that, in one embodiment, is centered at the previous location of the marker 104. The tracking gate is expanded only if the tracking algorithm can not locate the marker 104 within the gate. As an example, consider the situation when the previously determined location of a particular marker 104 is image element (50,50) in a video frame. If the tracking gate were limited to a 50 by 50 area of the video frame, then the tracking gate for this example would comprise the image elements bound within the area defined by the coordinates (25,25), (25,75), (75,25), and (75,75). The other portions of the video frame are searched only if the marker 104 is not found within this tracking gate.

According to one embodiment, the pixel coordinates of each marker in the video frame are tracked. The distance in the pixel domain between the two markers for each video frame is thereafter measured. The known physical distance of the two markers is divided by the measured distance to provide the scale factor for transforming the incremental motion of the block in the direction of the line connecting the two markers. This scale factor is updated for each new video frame and is used to transform the incremental motion of each marker from pixel domain to the physical domain. The transformation accounts for changes in the camera viewing angle, marker block orientation, and its distance to the camera during motion tracking.

The output of the process of FIGS. 3a and 3b comprises position and orientation data for the object 102. In another embodiment, the position and orientation of a specific part of the object 102, such as the tip of a biopsy needle, is obtained. The position and orientation of a specific part of the object 102 is determined by using previously surveyed reference data that provides the position of the specific part of the object 102 relative to the markers 104 in the reference coordinate system. A geometric transformation can be conducted that uses the reference data for the specific part of the object 102 in combination with the positions of the markers 104 accepted to determine the position and orientation of the specific part of the object 102 in the measurement coordinate system.

In an embodiment of the invention, the device 102 comprises a pointer device having a pointer tip 308. The position of the pointer tip 308 in the measurement coordinate system is determined as described above. The 3-dimensional path traced out by the pointer tip 308 can then be determined by monitoring the position of pointer tip 308 in successive images taken by camera 108. In an embodiment of the invention, this method and device can be used in 3-dimensional profiling of a patient, which involves measuring 3-dimensional contours on the surface of a patient. The pointer tip can be traced over the patient's skin in a desired path to determine the contours of the patient along that path. Patient profiling is useful, for example, for radiation treatment planning. It should be apparent to those skilled in the art that the invention can be used for any application requiring the determination of the locations and geometries of points, contours, or surfaces in three dimensions.

In another embodiment of the invention, the device 102 comprises a surgical instrument such as a biopsy needle. The position and orientation of the tip of the instrument 308 is monitored in the measurement coordinate system. This monitoring allows a practitioner to know the position of the tip 308 when it is inside a patient's body and cannot be seen. The monitoring of the tip's 308 orientation allows a practitioner to know the direction that the tip 308 will proceed as it is inserted into a patient's body.

In an embodiment, an illumination source is used with camera 108 (which is an infrared source in an embodiment) that projects light at the object 102. The generated light is reflected from one or more markers 104 on or attached to the marker block 150. The camera 108 captures and detects the reflected light from the one or more markers 104. The position, number, and orientation of the markers 104 are selected based upon the particular device 102 or system configuration being used.

In one embodiment, each marker 104 comprises a reflective or retro-reflective material that reflects light, whether in the visible or invisible wavelengths. If the illumination source is co-located with camera 108, then marker 104 preferably comprises a retro-reflective material that reflects light mostly in the direction of the illumination source. Alternatively, each marker 104 comprises its own light source. The marker 104 is used in place of or in conjunction with physical landmarks on the device 102 that is imaged by the camera 108 to detect position and movement. Markers 104 are preferably used instead of landmarks because such markers 104 can be detected and tracked more accurately via the video image generated by camera 108. Because of the reflective or retro-reflective qualities of the preferred markers 104, the markers 104 inherently provide greater contrast in a video image to a light detecting apparatus such as camera 108, particularly when the camera 108 and illumination source are co-located.

According to an embodiment, digital video recordings of the patient in a session can be recorded via camera 108. The same camera 108 used for tracking patient movement can be used to record video images of the patient for future reference. A normal ambient light image sequence of the patient can be obtained in synchronization with the measured movement signals of markers 104.

In one embodiment, a marker block is employed having a plurality of reference locations or markers 104 on one or more of its surface. Each reference location on the marker block preferably comprises a retro-reflective or reflective material that is detectable by an optical imaging apparatus, such as camera 108. One embodiment of the marker block 1471 utilizes multiple markers 1475 on a rigid hollow and light plastic block 1477 as shown in FIG. 5c.

A marker block can be formed into any shape or size, as long as the size, spacing, and positioning of the reference locations are configured such that a camera or other optical imaging apparatus can view and generate an image that accurately shows the positioning of the marker block.

Figure 5A:
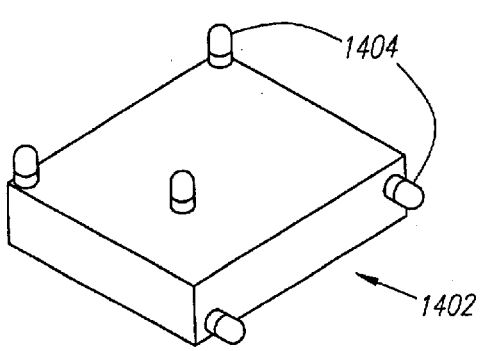
FIGS. 5a–c, 6, and 7 depict marker blocks according to embodiments of the invention.
Figure 5B:
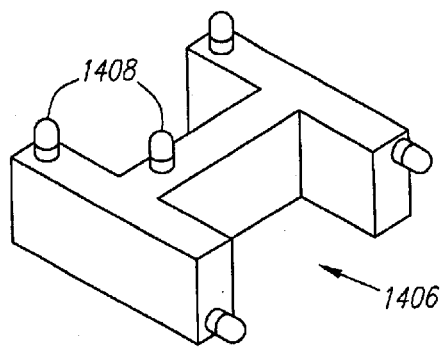
Figure 5C:
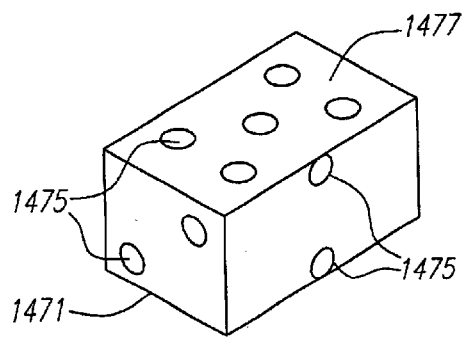

FIGS. 5a and 5b depict other embodiments of marker blocks 1402 and 1406 usable in the invention. Marker block 1402 includes a rectangular shape having multiple reflective or retro-reflective marker elements 1404 located on it. Marker block 1402 supports a rigidly mounted set of markers. The markers should appear as high contrast features in a real-time imaging device such as a video camera whose images are digitized and processed by a computer system. This realization of the marker block employs retro-reflective material covering a set of diameter spheres glued or otherwise attached to a rigid plastic box or platform. Marker block 1406 includes a non-rectangular structure having multiple reflective or retro-reflective marker elements 1408 located on it.

Figure 6:
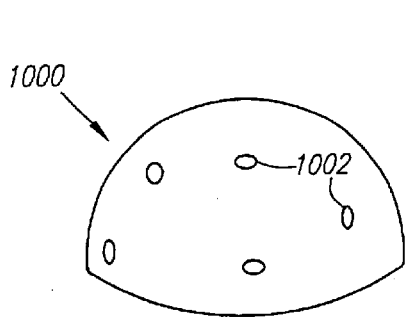
Figure 7:
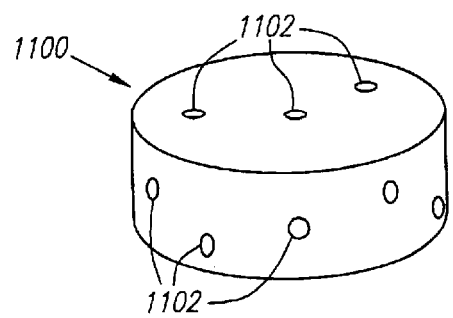

FIG. 7 depicts alternate embodiment of a marker block 1100 having a cylindrical shape with multiple reference locations comprised of retro-reflective elements 1102 located on its surface. Marker block 100 can be formed as a rigid block (e.g., from plastic). Blocks made in this fashion can be reused a plurality of times, even with multiple patients, e.g., if the normal hospital anti-infection procedures are followed. FIG. 6 depicts an alternate marker block 1000 having a hemispherical shape comprised of a plurality of retro-reflective elements 1002 attached to its surface.

The marker block can be formed with shapes to fit particular devices and instruments. For example, marker blocks can be implemented using molds or casts that match to specific locations on a device/instrument. Alternatively, the marker blocks can be formed to fit certain fixtures that are attached to a device or instrument. In yet another embodiment, the devices and instruments are formed with integral marker block(s) having reflective or retro-reflective markers on them.

In the foregoing specification, the invention has been described with reference to specific embodiments thereof. It will, however, be evident that various modifications and changes may be made thereto without departing from the broader spirit and scope of the invention. For example, the operations performed by image processing unit 110 can be performed by any combination of hardware and software within the scope of the invention, and should not be limited to particular embodiments comprising a particular definition of "image processing unit". The specification and drawings are, accordingly, to be regarded in an illustrative rather than restrictive sense.

What is claimed is:

1. A method for tracking a location and orientation of an object in three-dimensional space, comprising:
    (a) surveying a plurality of markers on an object;
    (b) calibrating an imaging device that is used to image the object;
    (c) obtaining a first set of object position and orientation data;
    (d) projecting the markers to an image domain to obtain coordinates of projected markers;
    (e) obtaining an image frame data set using the imaging device, the image frame data set comprising image data for at least three markers from the plurality of markers;
    (f) analyzing the image frame data set against the projected marker coordinates;
    (g) adjusting the first set of object position and orientation data if results of (f) are not within acceptable threshold tolerances; and
    (h) accepting the first set of object position and orientation data for the object if results of (f) are within the acceptable threshold tolerances.

2. The method of claim 1 in which the act of surveying the plurality of markers is performed in a reference coordinate space specific to the object.

3. The method of claim 2 in which survey data provides known relative positioning between the plurality of markers on the object.

4. The method of claim 1 in which the act of calibrating the imaging device is performed by translating and rotating the coordinate system for the imaging device relative to a measurement coordinate system.

5. The method of claim 4 which the measurement coordinate system is derived relative to a system isocenter of a medical device.

6. The method of claim 4 in which the act of calibrating is performed by imaging a structure of known location and dimensions.

7. The method of claim 1 in which the first set of object position and orientation data comprises an initial estimate of expected object position and orientation.

8. The method of claim 1 in which the act of projecting the markers uses position and orientation estimate from a prior image frame.

9. The method of claim 1 in which the first set of object position and orientation data comprises of six degrees of freedom (6 DOF) data values relating to the object.

10. The method of claim 1 in which the act of obtaining the image frame data set is repeated until at least three markers can be identified in the image frame data set.

11. The method of claim 1 in which marker coordinates are derived by image analysis from the image frame data set.

12. The method of claim 11 in which the act of (f) comprises forming a difference vector between projected marker coordinates of (d) and a second set of marker coordinates derived from (e).

13. The method of claim 12 in which the difference vector is compared against an acceptable threshold tolerance.

14. The method of claim 11 in which (g) comprises adjusting object 6 DOF estimate using the difference vector in such a manner to reduce the difference vector length.

15. The method of claim 1 in which the first set of object position and orientation data comprises a prior set of object position and orientation data.

16. The method of claim 1 further comprising:
    surveying relative positioning between the object and a device rigidly attached to the object.

17. The method of claim 1 in which an ultrasound probe is attached to the object, wherein positioning is determined for a structure imaged by the ultrasound probe.

18. The method of claim 17 in which the structure imaged by the ultrasound probe is translated and rotated into the measurement coordinate space.

19. The method of claim 18 in which mapping information is employed to perform the act of translating.

20. The method of claim 19 in which the mapping information is obtained by calibrating the ultrasound probe into the system coordinate space.

21. The method of claim 19 in which the mapping information is obtained by imaging a known structure using the ultrasound probe.

22. The method of claim 17 in which voxels generated by the ultrasound probe are mapped to object reference coordinates.

23. The method of claim 1 in which only a single imaging device is used to track the location and orientation of the object.

24. The method of claim 1 in which the coordinates of (d) comprise pixel coordinates.

25. The method of claim 1 in which the object comprises a marker block.

26. The method of claim 1 in which (g) is repeated until (h) is performed to accept the first set of object position and orientation data.

27. The method of claim 1 in which a surgical instrument with a tip is attached to the object, wherein tip position is calculated based upon the object position and orientation.

28. The method of claim 27 in which the tip is traced over a structure, wherein the structure is profiled based upon the tip position during tracing.

29. The method of claim 28 in which the structure comprises a patient.

30. A single camera method for tracking a location and orientation of an object, comprising:

surveying a set of markers on an object;

obtaining an estimate of the position and orientation of the object;

using a single camera to image the object to obtain an image frame to generate actual coordinate information, wherein at least three markers in the image frame are identifiable;

analyzing the actual coordinate information; and accepting the estimate of the position and orientation of the object if the result of analyzing the actual coordinate information is within an acceptable threshold tolerance.

* * * * *